United States Patent [19]

Grundei et al.

[11] 4,178,641
[45] Dec. 18, 1979

[54] KNEE-JOINT-ENDOPROTHESE

[75] Inventors: Hans Grundei; Wolfram Thomas, both of Lübeck, Fed. Rep. of Germany

[73] Assignee: Schutt and Grundei O.H.G., Lubeck, Fed. Rep. of Germany

[21] Appl. No.: 856,226

[22] Filed: Dec. 1, 1977

[30] Foreign Application Priority Data

Jan. 26, 1977 [DE] Fed. Rep. of Germany ....... 2703059

[51] Int. Cl.² ............................................... A61F 1/24
[52] U.S. Cl. ................................... 3/1.911; 128/92 C
[58] Field of Search ................................. 3/1.9–1.911; 128/92 C

[56] References Cited

U.S. PATENT DOCUMENTS

| 3,765,033 | 10/1973 | Goldberg et al. | 3/1.911 |
| 3,774,244 | 11/1973 | Walker | 3/1.911 |
| 3,816,855 | 6/1974 | Saleh | 3/1.911 |

*Primary Examiner*—Ronald L. Frinks
*Attorney, Agent, or Firm*—Kinzer, Plyer, Dorn & McEachran

[57] ABSTRACT

This invention relates to knee-joint endoprostheses, and provide an endoprosthetic member embodying condylar replacement surface means to simulate the natural slideway for the knee cap, said slideway defining a space for the cruciate ligaments of the natural joint, and also having a curved boundary to be brought into alignment with the transverse edge of the natural joint which forms the upper boundary of the space for the cruciate ligaments relative to the intercondylar eminence. The prosthesis for the inner tibial plateau is made concave and the prosthesis for the outer tibial plateau is made saddle-shaped to match the natural tibial plateaus, all the prosthetic parts being made from a wear-resistant plastics material such as polyethylene for example.

More generally, the invention provide an endoprosthetic condylar surface member comprising a shell of wear-resistant plastics material having a cupped shape connected to a slideway projecting laterally therefrom or alternatively the shell may comprise two cup-shaped parts interconnected by a slideway bridging piece.

4 Claims, 7 Drawing Figures

KNEE-JOINT-ENDOPROTHESE

BACKGROUND OF THE INVENTION

The present invention relates to a knee-joint endoprosthesis which enables at least one of the condyles of the thigh-bone or femur (the sliding parts of the femur) to be replaced by a wear-resistant member embodying condylar replacement surface means, in the form of a sliding or rolling pad for anchoring in the femoral bone to make good a damaged part of the femur, and which enables one or both of the associated plateaus on the shin-bone or tibia to be replaced, in accordance with the depth of the wear, by a replacement part made of wear-resistant plastics material. It is to be understood that the word "pad" as herein used has approximately the same or a similar connotation to the word "pad" when used to define the surface of an animal's paw that comes into contact with the ground.

Hitherto, known knee-joint endoprostheses have been so designed that damaged portions of the condyles of the thigh-bone are replaced by sliding pads of wear-resistant material which are anchored in cavities made in the condyles by means of spigots, ribs or the like. The lateral boundary faces of each pad in its extent from front to rear are parallel and in the longitudinal and transverse directions each pad is curved, two parallel pads being connected rigidly together by a yoke in the upper frontal area in cases where both femoral condyles are damaged. This means that the upper frontal portion of the pad does not rest flat against what remains of the natural femoral condyles and results in ridges which the knee cap has to cross when the joint is moved, which is painful. In addition, the parallel position of the pads hampers rotary movement of the shin-bone relative to the thigh bone. Furthermore, in known prostheses the tibial plateaus which replace the similarly worn tibial surfaces are made flat, so that as a result no proper bending and rotary movement of the bones relative to one another is possible as it is in the natural knee-joint.

It is an object of the invention to produce an endoprosthetic member for the femoral condyles and tibial plateaus which conform to the natural parts, in such a way that proper painless movement of the joint is possible with a smooth and unhampered sliding movement of the knee cap.

SUMMARY OF THE INVENTION

Accordingly, the invention consists in a knee-joint endoprosthetic member embodying condylar replacement surface means to simulate the natural slideway for the knee cap, said slideway defining a space for the cruciate ligaments of the natural joint and a curved boundary to be brought into alignment with the transverse edge of the natural joint which forms the upper boundary of the space for the cruciate ligaments relative to the intercondylar eminence, and wherein the prosthesis for the inner tibial plateau is made concave and the prosthesis for the outer tibial plateau is made saddle-shaped to match the natural tibial plateaus, said members being made from a wear-resistant plastics material.

The surface means may be in one or two parts. What is achieved by this replacement for natural femoral condyles and tibial plateaus in very much their natural form and by the slideway which is connected to the surface means or parts thereof and by the fact of lining up the curved boundary of the slideway between the surface means parts is, on the one hand, that the knee-cap is guided painlessly and on the other, that when the knee-joint is bent, the femoral condyles can slide or roll properly over the tibial plateaus as in a natural joint, it also being possible for the shin bone to perform rotary movements relative to the thigh bone without difficulty since the inner femoral condyle enters the concave tibial plateau and in practice forms a fixed pivot point about which the outer femoral condyle is able to move over the saddle shaped face of the outer tibial plateau. It is understood that the knee-joint prostheses are adapted to mean dimensions of a natural knee-joint and slight divergences can be compensated for by filling in with bone cement. With the way of achieving the object according to the invention, the tibial prostheses also are so formed that the surface of the inner plateau merges without a step into the surface of the intercondylar eminence as a result of its concavity and the surface of the outer plateau merges into the eminence without a step as a result of its saddle-shaped configuration, the thickness of the tibial prostheses naturally having to be matched to the depth to which the natural parts of the tibia have been destroyed.

BRIEF DESCRIPTION OF THE DRAWINGS

In order that the invention may be more clearly understood, reference will now be made to the accompanying drawings which show certain femoral and tibial embodiments by way of example only and in which.

DETAILED DESCRIPTION OF PREFERRED EMBODIMENTS

Figure 1:
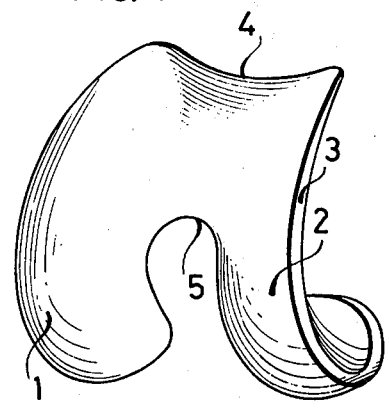
FIG. 1 is a perspective view of the femoral condyles of a prosthesis for the left knee-joint.

The drawings show an endoprosthesis for the left knee-joint, and it will be understood that a corresponding view for the right knee would be a mirror image of those drawings.

In accordance with the invention and as shown in the drawings, a pad 1 which acts as a prosthesis for the natural inner condyle of the thigh bone is faithfully copied from nature and has a somewhat banana shape. The second pad 2, which is a similarly faithful copy of the natural outer femoral condyle, in contrast terminates at a straight outer edge 3. The two pads 1 and 2 are connected together by a slideway 4 which merges in a smooth curve into the curves of the pads 1 and 2, which in cross-section are likewise of curved shape. The slideway 4 for the knee cap is provided between the pads 1 and 2, i.e. at the side where the space for the cruciate ligaments exists in the natural joint, with a curved boundary 5.

On the face adjoining the thigh bone, the two pads 1 and 2 are provided with rib-like longitudinally extending lugs 6 and 7. These lugs 6 and 7 are to enagage in groove-like cavities of suitable depth excavated from the natural femoral condyles and are inset in them in bone cement to prevent the femoral prosthesis from turning or moving. After the lugs have been engaged in the cavities, the prosthesis is moved and pressed home so that the boundary 5 is brought into line with the always sharply defined upper edge of the natural space for the cruciate ligaments, which edge forms the upper boundary of the space relative to the intercondylar eminence. In this way the prosthesis consisting of the femoral condyles 1 and 2 and the slideway 4 for the knee cap always takes up the fixed position which is essential to allow the joint to bend and stretch without hindrance and to provide sliding guidance for the knee cap over the full range of bending and stretching of the knee joint. The prosthesis is made from any wear-resistant plastics material found suitable such as polyethylene.

Figure 6:
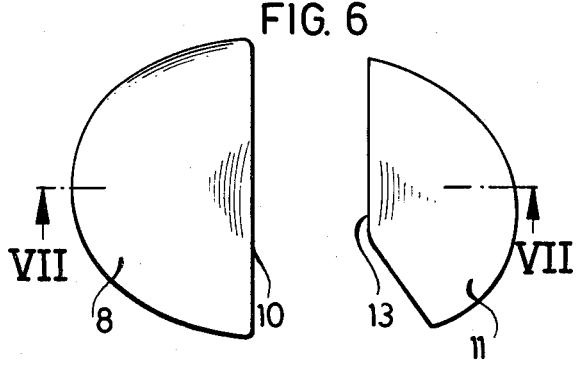
FIG. 6 is a plan view of the tibial prostheses.
Figure 7:
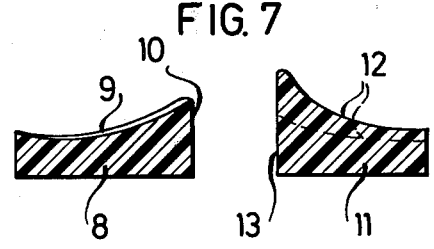
FIG. 7 is a section on line VII—VII of FIG. 6.

Since in addition to the femoral condyles the tibial plateaus on the shin bone will also be damaged or worn, they too must be replaced by a prosthesis at the same time as the femoral condyles. The thickness of these tibial prostheses depends on the depth to which the natural tibial plateaus have been damaged. For the inner femoral pad 1, the tibial prosthesis 8 is concave on its surface 9, as can be seen in FIGS. 6 and 7, and is provided with a straight inner edge 10, the surface 9 merging at the straight edge 10 into the surface of the intercondylar eminence, which does not wear, without a step.

The tibial prosthesis 11 for the outer femoral pad 2 on the other hand is provided with a saddle shaped surface 12, which similarly merges at the upper inner edge into the intercondylar eminence of the natural joint without a step. In this case too the inner edge 13 is straight and flat.

The two tibial prostheses 8 and 11, which are also advantageously made from a suitable wear-resistant plastics material, e.g. polyethylene, are inserted in trough-shaped cavities excavated from the upper surface of the shin bone and are secured by using bone cement. To allow equality of height and parallelism to be checked by X-ray, metal graticles are incorporated in the inner edges 10, 13 of the plateau. The tibial prosthesis 8 forms a concave bearing surface for the femoral pad 1, which thus occupies a substantially fixed position when the shin bone turns relative to the thigh bone, the outer femoral pad sliding over the saddle shaped surface 12 of the outer tibial prosthesis 11.

When the knee-joint endoprosthesis performs a bending or stretching movement, the points at which the femoral pads 1 and 2 slide or roll over the tibial plateaus 8, 11 are always at substantially the same level, thus preventing the joint from tilting sideways. The curvature of the femoral pads in the longitudinal direction is formed accodingly, as in nature.

Figure 2:
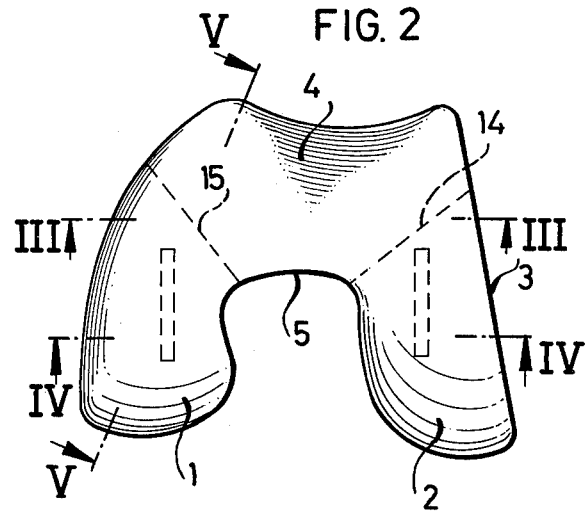
FIG. 2 is an elevation view of the femoral condyles shown in FIG. 1.
Figure 5:
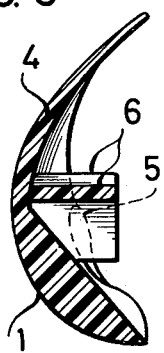
FIG. 5 is a cross-section on line V—V of FIG. 2.
Figure 3:
FIG. 3 is a cross-section on line III—III of FIG. 2
Figure 4:
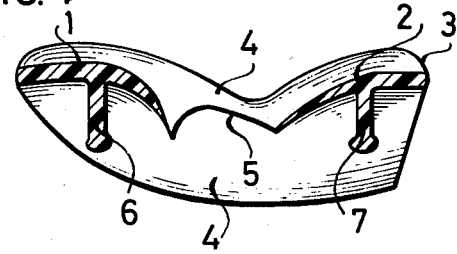
FIG. 4 is a cross-section on line IV—IV of FIG. 2.

In cases where only one femoral condyle e.g. the inner one, and the associated tibial plateau are worn, only the inner pad 1 and the tibial prosthesis 8 need to be provided as a prosthetic replacement. The pad 2 is then omitted up to the broken line 14 (FIG. 2). Similarly, if the outer femoral condyle and the outer tibial plateau are worn, only the outer femoral pad 2 and the tibial prosthesis 11 are required, i.e. the pad 1 is omitted up to the broken line 15. In both these cases however the slideway 4 for the knee cap is still connected either to pad 2 or pad 1, so that firstly the position of the prosthesis on the thigh bone can be definitely fixed by reference to the inner edge 5 and secondly so that a proper ridge free slideway is always available for the knee cap.

Reference is herein made to wear-resistant plastics material exemplified as polyethylene, since this has been found suitable in practice for the tibial prosthesis.

However, other known materials are under test and it is believed that the following may also be suitable for this purpose viz polymethyl methacrylate,
polypropyl methacrylate,
Co-polymers of methyl methacrylate and
N-Butyl methacrylate,
the partial ester of the copylmer of styrene and
maleic anhydride, and
copolymers of ethylene and proplylene.

We claim:

1. A knee-joint endoprosthetic member embodying condylar replacement surface means to simulate the natural slideway for the knee cap, said slideway defining a space for the cruciate ligaments of the natural joint, and a curved boundary to be brought into alignment with the transverse edge of the natural joint which forms the upper boundary of the space for the cruciate ligaments relative to the intercondylar eminence, and wherein the prosthesis for the inner tibial plateau is made concave and the prosthesis for the outer tibial plateau is made saddle-shaped to match the natural tibial plateaus, said members being made from a wear-resistant material.

2. An endoprosthetic member according to claim 1, wherein in plan the surface means part for the inner femoral condyle is approximately banana-shaped from front to rear and in cross-section is curved, curving at a steeper angle towards the space for the cruciate ligaments of the natural joint, while the surface means part for the outer femoral condyle has substantially straight outer edge in plan while its part of curved cross-section which forms the outer femoral condyle is inwardly inclined towards the space for the cruciate ligaments at a less steep angle.

3. An endoprosthetic member according to claim 1, in conjunction with a tibial plateau prosthesis, the surfaces of said surface means for the femoral condyles being so formed that the slide and roll points always remain at substantially the same level when the natural knee-joint is moved.

4. An endoprosthetic member according to claim 1, wherein on its side adjacent the thigh bone, said member has lug means which are directed from front to rear and which are adapted to be cemented into cavities made in the natural femoral condyles.

* * * * *